(12) United States Patent
Zhang et al.

(10) Patent No.: US 11,724,112 B2
(45) Date of Patent: Aug. 15, 2023

(54) BIOSTIMULATOR HEADER ASSEMBLY HAVING INTEGRATED ANTENNA

(71) Applicant: PACESETTER, INC., Sylmar, CA (US)

(72) Inventors: Bei Ning Zhang, Pasadena, CA (US); Brett C. Villavicencio, Valencia, CA (US); Perry Li, Arcadia, CA (US); Souvik Dubey, Woodland Hills, CA (US)

(73) Assignee: PACESETTER, INC., Sylmar, CA (US)

( * ) Notice: Subject to any disclaimer, the term of this patent is extended or adjusted under 35 U.S.C. 154(b) by 120 days.

(21) Appl. No.: 16/951,907

(22) Filed: Nov. 18, 2020

(65) Prior Publication Data

US 2021/0187310 A1 Jun. 24, 2021

Related U.S. Application Data

(60) Provisional application No. 62/949,996, filed on Dec. 18, 2019.

(51) Int. Cl.
| | |
|---|---|
| *A61N 1/375* | (2006.01) |
| *A61N 1/372* | (2006.01) |
| *A61N 1/05* | (2006.01) |
| *H01Q 1/40* | (2006.01) |
| *H01Q 7/00* | (2006.01) |

(52) U.S. Cl.
CPC ....... *A61N 1/37229* (2013.01); *A61N 1/0573* (2013.01); *A61N 1/3756* (2013.01); *A61N 1/3758* (2013.01); *A61N 1/37512* (2017.08); *A61N 1/37518* (2017.08); *H01Q 1/40* (2013.01); *H01Q 7/00* (2013.01)

(58) Field of Classification Search
CPC .............. A61N 1/37229; A61N 1/0573; A61N 1/37512; A61N 1/37518; A61N 1/3756; A61N 1/3758
See application file for complete search history.

(56) References Cited

U.S. PATENT DOCUMENTS

| | | | |
|---|---|---|---|
| 2015/0097734 A1* | 4/2015 | Zhao | H01Q 11/08 29/601 |
| 2016/0213937 A1 | 7/2016 | Reinke et al. | |
| 2017/0281955 A1 | 10/2017 | Maile et al. | |
| 2018/0056080 A1 | 3/2018 | Reinke et al. | |
| 2018/0133487 A1* | 5/2018 | Shah | A61N 1/3754 |
| 2019/0030346 A1 | 1/2019 | Li et al. | |

(Continued)

*Primary Examiner* — Eugene T Wu
(74) *Attorney, Agent, or Firm* — Womble Bond Dickinson (US) LLP

(57) ABSTRACT

A biostimulator, such as a leadless cardiac pacemaker, having a header assembly that includes an antenna, is described. The antenna can be integrated into an insulator that separates an electrode of the header assembly from a flange of the header assembly. The antenna includes an antenna loop embedded in a ceramic material of the insulator. The antenna loop is located distal to the flange to reduce the likelihood of signal interference and increase communication range of the antenna. The header assembly is mounted on a housing have an electronics compartment, and an antenna lead extends from the antenna loop to electronic circuitry contained within the electronics compartment. Other embodiments are also described and claimed.

20 Claims, 4 Drawing Sheets

(56) References Cited

U.S. PATENT DOCUMENTS

| | | |
|---|---|---|
| 2019/0038905 A1 | 2/2019 | Régnier |
| 2019/0134412 A1 | 5/2019 | Shuros et al. |
| 2021/0046310 A1* | 2/2021 | Griffith .............. A61N 1/36038 |

* cited by examiner

BIOSTIMULATOR HEADER ASSEMBLY HAVING INTEGRATED ANTENNA

This application claims the benefit of priority to U.S. Provisional Patent Application No. 62/949,996 entitled "BIOSTIMULATOR HEADER ASSEMBLY HAVING INTEGRATED ANTENNA" filed on Dec. 18, 2019, and that patent application is incorporated herein in its entirety.

BACKGROUND

Field

The present disclosure relates to biostimulators. More specifically, the present disclosure relates to leadless biostimulators having header assemblies.

Background Information

Cardiac pacing by an artificial pacemaker provides an electrical stimulation to the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart.

Conventional pacemakers have several drawbacks, including complex connections between the leads and the pulse generator, and a risk of infection and morbidity due to the separate leads and pulse generator components. Self-contained and self-sustainable biostimulators, or so-called leadless biostimulators, have been developed to address such drawbacks. A leadless biostimulator has no connections between the pulse generator and a lead. Furthermore, the leadless biostimulator can be attached to tissue within a dynamic environment, e.g., within a chamber of a beating heart, with reduced likelihood of infection. Accordingly, leadless biostimulator technology represents the latest advancement in pacemaker technology. The leadless biostimulator can interact with the tissue using a header assembly, which typically includes a fixation mechanism to attach to the tissue and an electrical feedthrough to deliver electrical impulses from the pulse generator to the tissue.

SUMMARY

Existing leadless biostimulators could benefit from the ability to communicate data, such as performance information, from the implanted biostimulator to a device external to the patient. To enable such communication, an antenna can be integrated into the leadless biostimulator. It may be undesirable, however, to integrate the antenna if it requires an increase in a size of the biostimulator. For example, the antenna may require an increase to the size of a biostimulator housing, which may negatively impact device implantation and/or performance. Compactness of implantable devices is paramount, and thus, there is a need to integrate the antenna within the biostimulator without changing the form factor of the biostimulator.

A biostimulator having an antenna to wirelessly communicate signals is provided. The antenna is integrated into an insulator of a header assembly, and thus, does not require enlargement of the biostimulator form factor. The insulator can include, for example, a ceramic material, and the antenna can be a monopole antenna embedded within the ceramic material.

The biostimulator can include a housing having an electronics compartment, and the header assembly can be mounted on the housing. More particularly, the header assembly can include a flange, and the flange can be mounted on the housing to enclose the electronics compartment. Electronic circuitry, such as communication circuitry, can be located within the electronics compartment. In an embodiment, the antenna has an antenna lead that connects to the electronic circuitry. The antenna can be embedded within the insulator of the header assembly, and thus, the antenna lead can extend from the electronic circuitry contained within the electronics compartment through the insulator to one or more antenna loops.

In an embodiment, the insulator includes an insulator wall extending around an insulator cavity. The insulator cavity extends along a longitudinal axis from an insulator distal end of the insulator wall to an insulator proximal end of the insulator wall. An electrode of the header assembly can be disposed within the insulator cavity. The antenna has one or more antenna loops embedded in the insulator wall between the insulator distal end and the insulator proximal end. Thus, the antenna loop(s) can extend around the electrode. The antenna loop(s) can include one or more open loops. For example, the one or more open loops can include several open loops extending around the longitudinal axis. In an embodiment, one or more of the antenna loop(s) are located distal to the flange of the header assembly, and thus, the flange does not interfere with communication by the antenna loop(s).

In an embodiment, the header assembly includes a helix mount mounted on the flange. The header assembly can also include a gasket. The gasket can have an annular body extending around the electrode. The annular body may be resiliently compressed between the helix mount and one of the flange or the insulator. In an embodiment, the gasket is resiliently compressed between the helix mount and the flange. In an embodiment, the gasket is resiliently compressed between the helix mount and the insulator. The gasket prevents liquid ingress that could interfere with device function.

In an embodiment, a distal section of the insulator wall of the insulator has a first transverse width larger than a second transverse width of a proximal section of the insulator wall. The antenna loop(s) can be embedded within the distal section, which can be located distal to the flange. The antenna lead can run through the proximal section, which can be located radially inward from the flange. Accordingly, the antenna lead can carry signals through the proximal section to the antenna loop(s) in the distal section for transmission.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
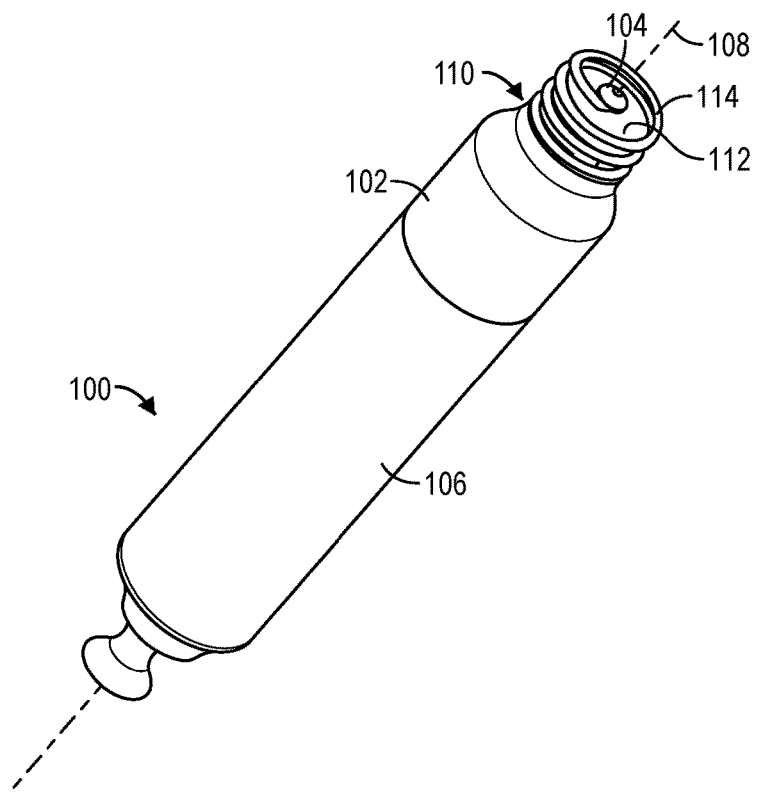
FIG. 1 is a perspective view of a biostimulator, in accordance with an embodiment.

Embodiments describe a biostimulator, e.g., a leadless pacemaker, having a header assembly that includes an antenna. The biostimulator may be used to pace cardiac tissue. Alternatively, the biostimulator may be used in other applications, such as deep brain stimulation. Thus, reference to the biostimulator as being a leadless cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodi-ment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator such as a leadless cardiac pacemaker is provided. The biostimulator includes an antenna integrated into a header assembly. More particularly, the antenna can be integrated into a feedthrough subassembly of the header assembly, e.g., by embedding the antenna within an insulator of the subassembly. Embedding the antenna within a ceramic material of the insulator allows integration of the antenna without increasing a form factor of the biostimulator. The insulator can separate a flange of the biostimulator from an electrode of the biostimulator, and at least a portion of the insulator can extend distal to the flange. Accordingly, the antenna can include one or more loops, e.g., open loops, embedded within the insulator distal to the flange. Positioning the one or more loops distal to the flange can reduce signal interference from the flange, which may increase a communication range of the antenna. The header assembly may include a gasket to prevent ingress of fluid into an internal volume of the biostimulator, and the gasket may be located outside of or inside of the insulator.

Referring to FIG. 1, a perspective view of a biostimulator is shown in accordance with an embodiment. A biostimulator 100 can be a leadless biostimulator, e.g., a leadless cardiac pacemaker. The biostimulator 100 can include an electrode 104 at a distal end of the device, and a proximal electrode 106 proximal to the electrode 104. The electrodes can be integral to a housing 102, or connected to the housing, e.g., at a distance of less than several centimeters from the housing 102. The housing 102 can contain an energy source to provide power to the pacing electrodes. The energy source can be a battery, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. In an embodiment, the energy source can be an energy harvesting device, such as a piezoelectric device that converts mechanical strain into electrical current or voltage. The energy source can also be an ultrasound transmitter that uses ultrasound technology to transfer energy from an ultrasound subcutaneous pulse generator to a receiver-electrode implanted on an endocardial wall.

The biostimulator 100 can have a longitudinal axis 108. The longitudinal axis 108 can be an axis of symmetry, along which several biostimulator components are disposed. For example, a header assembly 110 can be mounted on a distal end of the housing 102 along the longitudinal axis 108. The header assembly 110 can include an electrical feedthrough subassembly including an electrical feedthrough (not shown) and the electrode 104, e.g., a pacing tip. The header assembly 110 can also include a fixation subassembly. The fixation subassembly can include a helix mount 112. The helix mount 112 can be mounted on the electrical feedthrough subassembly around the longitudinal axis 108. In an embodiment, the fixation subassembly includes a fixation element 114 mounted on the helix mount 112 along the longitudinal axis 108. The assembled components of the biostimulator 100 can provide a distal region that attaches to a target tissue, e.g., via engagement of the fixation element 114 with the target tissue. The distal region can deliver a pacing impulse to the target tissue, e.g., via the distal electrode 104 that is held against the target tissue.

Figure 2:
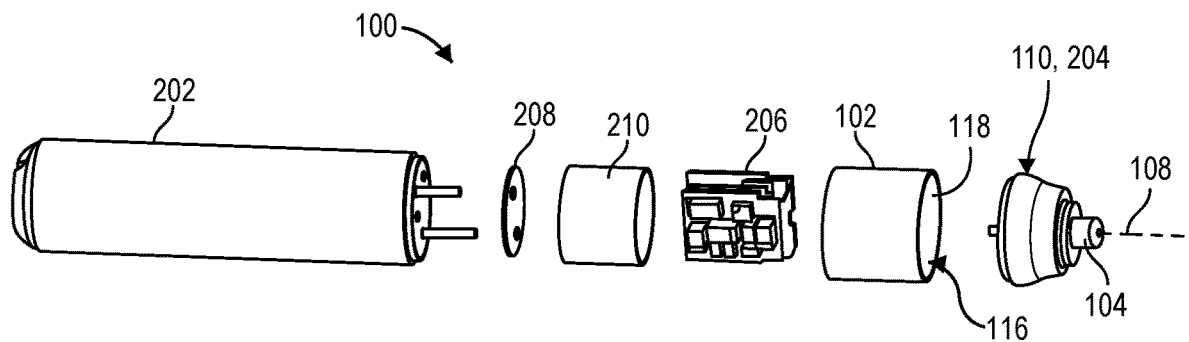
FIG. 2 is an exploded view of a biostimulator, in accordance with an embodiment.

Referring to FIG. 2, an exploded view of a biostimulator is shown in accordance with an embodiment. The housing 102 can contain an electronics compartment 116. More particularly, the housing 102 can have a housing wall, e.g., a cylindrical wall, laterally surrounding the electronics compartment 116. In an embodiment, the housing wall has an inner surface 118 extending around the electronics compartment 116 on the longitudinal axis 108. The housing wall can include a conductive, biocompatible, inert, and anodically safe material such as titanium, 316L stainless steel, or other similar materials, to laterally enclose the electronics compartment 116. The electronics compartment 116 can be axially enclosed at a proximal end by the battery 202. More particularly, a distal surface or face of the battery 202 can define the proximal end of the electronics compartment 116. The electronics component 116 can be axially enclosed at a distal end by the header assembly 110. More particularly, a proximal surface of a feedthrough subassembly 204 of the header assembly 110 can define the distal end of the electronics compartment 116. The housing 102 can be attached, e.g., welded, to the header assembly 110 and the battery 202. Accordingly, the electronics compartment 116 can be contained between the battery 202, the inner surface 118 of the housing 102, and the header assembly 110.

In an embodiment, electronic circuitry 206 is contained within the electronics compartment 116. The electronic circuitry 206 can include a flexible circuit assembly having a flexible substrate. One or more electronic components may be mounted on the flexible substrate. For example, the electronic circuitry 206 can include one or more passive electronic components, e.g., capacitors, and one or more active electronic components, e.g., processors. The electronic components can be interconnected by electrical traces, vias, or other electrical connectors. In an embodiment, the electronics assembly includes one or more electrical connectors, e.g., socket and pin connectors or metallized contact pads, to connect to the battery 202 and the electrical feedthrough subassembly 204. For example, a socket connector or a metallized pad can receive and/or connect to an electrode pin, a terminal pin, or an antenna lead, as described below.

To reduce the likelihood that the electrical connectors of the electronic circuitry 206 might accidentally short-circuit to other conductive components of the biostimulator 100, such as the housing 102 or battery 202, the biostimulator 100 may incorporate components to electrically insulate and/or protect the electronic components from short-circuiting. For example, the biostimulator 100 can include an end insulator 208. The end insulator 208 can include a planar structure formed from insulating material and sized to separate the electronic circuitry 206 from the energy source 202. The biostimulator 100 may also include a wall insulator 210. The wall insulator 210 can be a cylindrical sleeve formed from insulating material and sized to separate the electronic circuitry 206 from the inner surface 118 of the housing 102. Accordingly, the end insulator 208 and the wall insulator 210 can shroud the electronic circuitry 206 to reduce the likelihood of short circuiting between the electronic components and surrounding structures. It will be appreciated that the flexible substrate of the electronic circuitry 206 may provide insulation and separation from the housing 102 and/or the battery 202. For example, a distal end of the electronic circuitry 206 may be a fold that is entirely formed from insulating material, and thus, short circuiting between the distal end and the feedthrough subassembly 204 can be avoided.

The biostimulator components can form a hermetic enclosure around the electronic circuitry 206. For example, the battery 202, housing 102, and feedthrough subassembly 204 can be welded along mating seams at the proximal and distal ends of the housing 102 to hermetically seal the electronics compartment 116. The feedthrough subassembly 204 can provide an isolated electrical path from the electronic circuitry 206, which is hermetically sealed within the electronics compartment 116, to the electrode 104. More particularly, in an embodiment, the feedthrough subassembly 204 transmits afferent and efferent signals between the electronic circuitry 206 and a target tissue.

Figure 3:
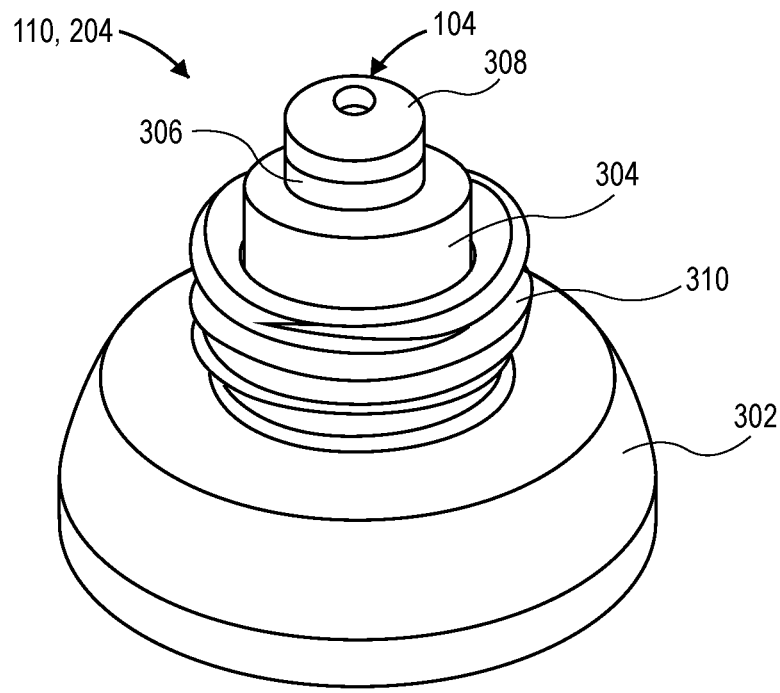
FIG. 3 is a perspective view of a feedthrough subassembly of a header assembly of a biostimulator, in accordance with an embodiment.

Referring to FIG. 3, a perspective view of a feedthrough subassembly of a header assembly of a biostimulator is shown in accordance with an embodiment. The electrical feedthrough subassembly 204 of the header assembly 110 can be a multifunction component. Unlike a traditional pacemaker where the electrical feedthrough is separated from the pacing site by a lead and functions solely to transfer power to the lead, the distal electrode 104 of the electrical feedthrough subassembly 204 of the biostimulator 100 may be in direct contact with the stimulation site and used to deliver impulses to the tissue. Additionally, the electrical feedthrough subassembly 204 can not only serve as the electrical pass-through from a hermetic package to a surrounding environment, but may also serve other functions, such as providing a housing for a steroid or other filler, or providing direct tissue interaction.

The feedthrough subassembly 204 can include several components having respective functions. A flange 302 of the subassembly can be connected to a case of the biostimulator 100. For example, the flange 302 can be mounted on and bonded to the housing 102 as described above. The subassembly can include an insulator 304 to electrically isolate the flange 302 from electrical components passing from the hermetic enclosure of the biostimulator 100 to the surrounding environment. For example, the insulator 304 can include and/or be formed from a ceramic material that insulates the flange 302 from the electrode 104. The electrode 104 can connect a pulse generator of the electronic circuitry 206 to a pacing tip. The flange 302, the insulator 304, and the electrode 104 can be connected by a brazed joint that hermetically seals the components and isolates the pacing tip on a distal end of the subassembly from a proximal end of the subassembly that connects to the electronic circuitry 206.

In certain implementations, the electrical feedthrough subassembly 204 can be an unfiltered assembly. More particularly, the configuration of the electrical feedthrough subassembly 204 can include an active component, e.g., the distal electrode 104, isolated from a ground component (e.g., the flange 302) by the insulator 304. The electrode 104 may include the pacing tip, which can include an electrode body 306 and/or an electrode tip 308. In implementations of the present disclosure, the electrode tip 308 may be mounted on the electrode body 306, e.g., on a distal end of the electrode body 306, as illustrated in FIG. 3. The electrode body 306 and electrode tip 308 can be welded together.

The insulator 304 can surround a portion of the electrode body 306. More particularly, the insulator 304 can contain and separate the conductive electrode body 306 from a mounting wall 310 of the flange 302. Both the electrode body 306 and the mounting wall 310 can be conductive. By contrast, the insulator 304 can be formed from an alumina ceramic or other insulating material. Accordingly, the insulator 304 can be located between the electrode body 306 and the mounting wall 310 to electrically insulate the distal electrode 104 from the flange 302. The mounting wall 310 can include a thread, e.g., an external thread on an outer surface, which may form a threaded connection between the electrical feedthrough subassembly 204 and a fixation subassembly of the header assembly 110. The fixation subassembly can include the helix mount 112 and the fixation element 114 mounted on the helix mount 112 (FIG. 1). In implementations in which the electrical feedthrough subassembly 204 is bonded, press-fit, or otherwise coupled to the helix mount 212, the thread may be omitted or the mounting wall 310 may include other surface features adapted for coupling the feedthrough subassembly 204 to the fixation subassembly to form the header assembly 110.

Figure 4:
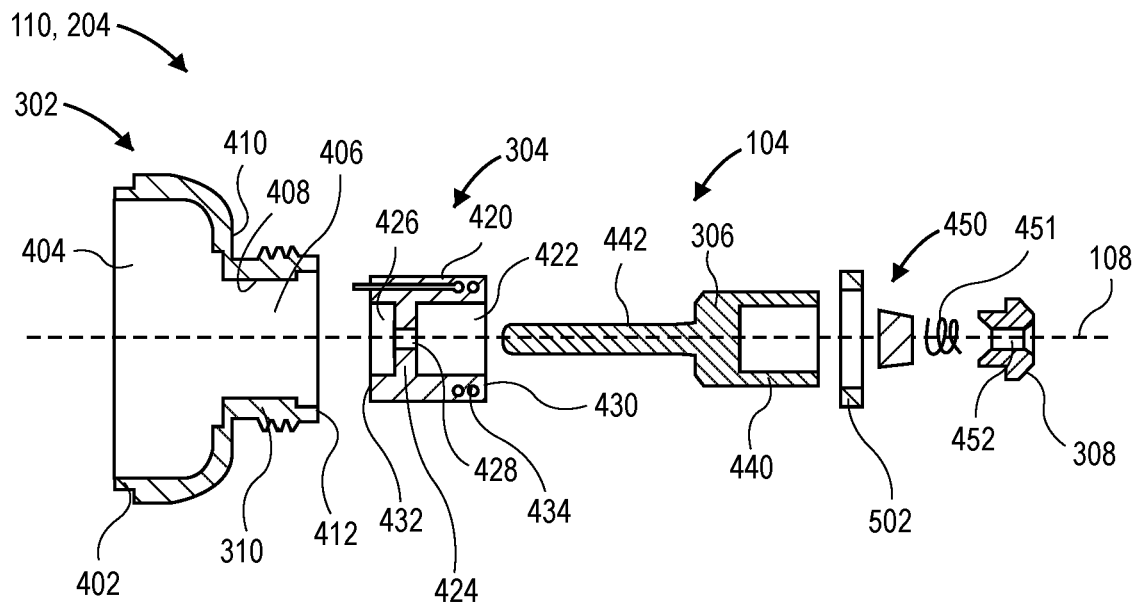
FIG. 4 is an exploded view of a feedthrough subassembly of a header assembly of a biostimulator, in accordance with an embodiment.

Referring to FIG. 4, an exploded view of a feedthrough subassembly of a header assembly of a biostimulator is shown in accordance with an embodiment. The flange 302 can include a mounting lip 402 to engage a distal end of the housing 102 (FIG. 1). A hermetic weld can be formed around the mounting lip 402 to seal the electronics compartment 116 between the flange 302 and the housing 102. In one implementation, the flange 302 includes a mounting hole 404 that, when the biostimulator 100 is assembled, extends distally from the electronics compartment 116 along the longitudinal axis 108 and through a distal surface of the flange 302 to a surrounding environment. More particularly, the mounting hole 404 provides a channel between the electronics compartment 116 and the surrounding environment.

The mounting wall 310 of the flange 302 can extend around the mounting hole 404. In an embodiment, the mounting wall 310 extends around a flange cavity 406 (a distal portion of the mounting hole 404). For example, an interior surface 408 of the mounting wall 310 can define the flange cavity 406. The flange cavity 406 can extend through the flange 302 from a flange shoulder 410 to a flange distal end 412 of the mounting wall 310.

In one implementation and as further illustrated in FIG. 4, the insulator 304 for the header assembly 110 of the biostimulator 100 has an insulator wall 420 extending around an insulator cavity 422. The insulator wall 420 can extend longitudinally from an insulator distal end 430 to an insulator proximal end 432. In one implementation, the insulator wall 420 can be cylindrical, having an outer diameter and an inner diameter; however, other insulator shapes may be used in other implementations of the present disclosure. The outer diameter of the insulator wall 420 can be sized to fit within the mounting hole 404 of the flange 208. More particularly, the insulator 304 can be disposed within, and can fill, the flange cavity 406 in the assembled state.

In certain implementations, the insulator 304 includes an insulator base 424 extending laterally within the insulator cavity 422 at a location between the insulator distal end 430 and the insulator proximal end 432. The insulator base 424 can be a transverse wall extending across the interior of the insulator 304, orthogonal to the longitudinal axis 108. More particularly, the insulator base 424 can be a transverse wall separating the insulator cavity 422 of the insulator 304 from a proximal cavity 426 of the insulator 304. The cavities 422, 426 may be radially inward from the insulator wall 420. In one implementation, an insulator hole 428 extends through the insulator base 424 along the longitudinal axis 108. The insulator hole 428 can interconnect the cavities 422, 426, and the interconnected hole and cavities can provide the insulator cavity 422 that extends along the longitudinal axis 108 from the insulator distal end 430 to the insulator proximal end 432. Accordingly, when the insulator 304 is mounted within the flange cavity 406 of the flange 208, and sealed to the flange 208 by a brazed joint, the insulator cavity 422 provides a channel between the electronics compartment 116 and the surrounding environment.

In an embodiment, the insulator 304 includes an antenna 434. The antenna 434 can be at least partly embedded within the insulator wall 420, as described below. The antenna 434 can be electrically connected to communication circuitry of the electronic circuitry 206, and thus, provides wireless communication from the biostimulator 100 to an external communication device. The antenna 434 configuration is described further below.

The electrode 104 of the feedthrough subassembly 204 in accordance with the present disclosure may include a monolithic electrode body 306. For example, the monolithic electrode body 306 can have several distinct portions that are integrally formed with each other. In one implementation, the electrode body 306 includes a cup 440 and a pin 442 that are integrally formed such that the electrode body 306 is monolithic, or, in other words, has a unitary or single-piece construction.

Figure 5:
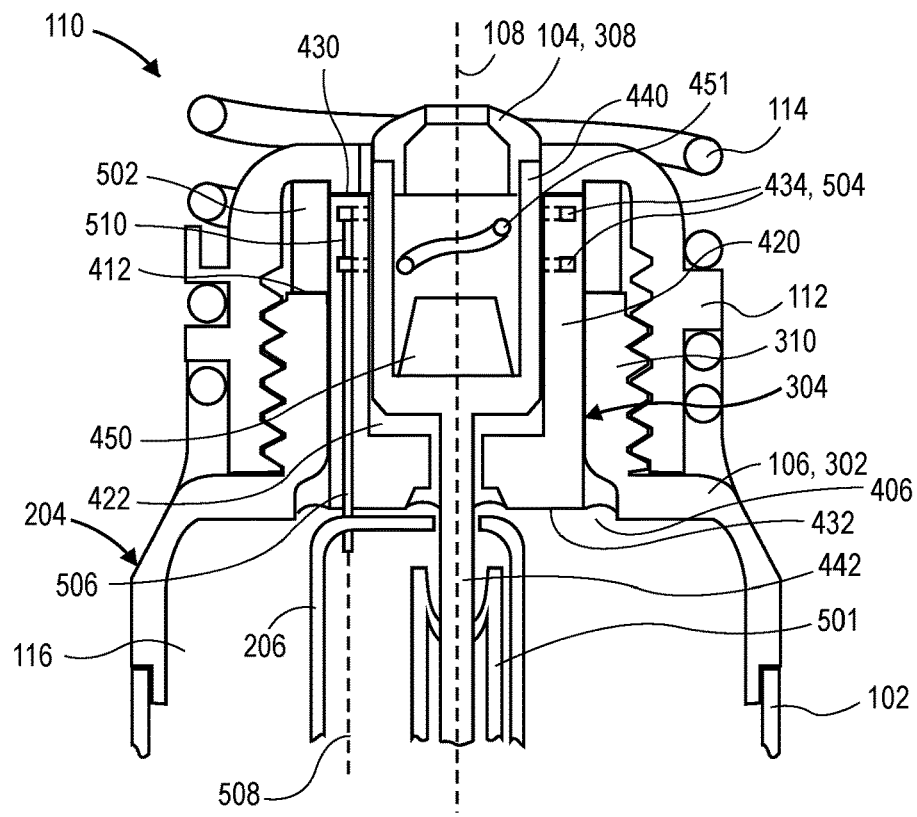
FIG. 5 is a cross-sectional view of a header assembly of a biostimulator, in accordance with an embodiment.

The electrode 104 can be sized to fit within the insulator cavity 422. For example, the pin 442 can be sized to fit through the insulator hole 428 of the insulator 304, and the cup 440 can be sized to fit within the insulator cavity 422 of the insulator 304 (FIG. 5). It will be appreciated that, when the electrode 104 is disposed within the insulator cavity 422, the antenna 434 embedded within the insulator wall 420 can extend around the electrode 104. For example, loops of the antenna 434 can extend circumferentially around the cup 440. When the electrode 104 is disposed within the insulator 304 and the flange 302, and sealed to the insulator 304 by a brazed joint, the monolithic electrode body 306 provides an electrical pathway from the electronics compartment 116 to the surrounding environment. Electrical impulses can be transmitted from the electronic circuitry 206 proximal to the insulator base 424 to the cup 440 distal to the insulator base 424. More particularly, the cup 440 and the pin 442 can serve as the electrically active path from the electronic circuitry 206 within the electronics compartment 116 to the patient-contacting pacing electrode tip 308.

The biostimulator 100, and more particularly the electrical feedthrough subassembly 204, can include a filler 450, such as a monolithic controlled release device (MCRD). By way of introduction and without limitation, the filler 450 may include a therapeutic material, and can be loaded into the cup 440. Accordingly, the filler 450 can deliver a specified dose of a therapeutic agent, e.g., a corticosteroid, into target tissue at an implantation site of the biostimulator 100 within a patient. In an embodiment, the filler 450 is retained at a proximal location within an interior cavity of the cup 440 by a retention spring 451. The retention spring 451 can press against a distal end of the filler 450 and a proximal end of the electrode tip 308 to urge the filler 450 away from the electrode tip 308 and reduce the likelihood of the filler 450 clogging a tip hole 452 of the electrode tip 308.

The electrode tip 308 can be mounted on the electrode body 306 after the filler 450 is loaded into the cup 440. In one implementation, the electrode tip 308 includes the tip hole 452 extending through the electrode tip 308 along the longitudinal axis 108. The tip hole 452 may provide a channel between the interior cavity of the cup 440 and the surrounding environment. Accordingly, therapeutic agent eluted by the filler 450 can pass through the retention spring 451 and the tip hole 452 to the target tissue at the implantation site of the biostimulator 100. In other implementations, the electrode tip 308 and/or the electrode body 306 may include other openings or ports through which fluid may enter and exit the cup 440. The electrode tip 308 can be conductive, and electrically in contact with the electrode body 306, such that pacing impulses transmitted through the electrode body 306 from the electronic circuitry 206 can travel through the electrode tip 308 to the target tissue.

In certain implementations, each of the components of the electrical feedthrough subassembly 204 may be symmetrically formed about the longitudinal axis 108. For example, the cross-sectional area of the insulator 304 illustrated in FIG. 4 can be swept about the longitudinal axis 108 such that the insulator wall 420 has a hollow cylindrical shape and the insulator base 424 has an annular disc shape. In other implementations, the profiles of the one or more of the components of the electrical feedthrough subassembly 204 may be non-symmetrical. For example, a cross-section of the electrode body 306 taken about a transverse plane extending orthogonal to the longitudinal axis 108 may reveal an outer surface of the pin 442 and/or the cup 440 that is square, pentagonal, elliptical, etc., or any other suitable shape. Accordingly, the particular shapes illustrated in the figures are provided by way of example only and not necessarily by way of limitation.

Referring to FIG. 5, a cross-sectional view of a header assembly of a biostimulator is shown in accordance with an embodiment. As described above, the housing 102 and a portion of the header assembly 110, e.g., the flange 302, can define the electronics compartment 116. The electronic circuitry 206 can be mounted in the electronics compartment 202, and may be in electrical communication with the feedthrough subassembly 204, e.g., the pin 442, through a socket connector 501 or another electrical connection.

The header assembly 110 includes the fixation subassembly mounted on the feedthrough subassembly 204. More particularly, the helix mount 112 can be mounted on the mounting wall 310 of the flange 302 to connect the subassemblies and form the header assembly 110. In one implementation, the fixation element 114 includes a helix mounted on the helix mount 112. The fixation element 114 can be suitable for attaching the biostimulator 100 to tissue, such as heart tissue. The helix can extend distally from the helix mount 112 about the longitudinal axis 108. For example, the helix can revolve about the longitudinal axis 108. The helix can include a spiral wire, formed by coiling or cut from a wall of a length of tubing, which extends in a rotational direction around the longitudinal axis 108. For example, the helix can revolve in a right-handed direction about the longitudinal axis 108. In the case of a right-handed spiral direction, the biostimulator 100 can be advanced into contact with a target tissue, and the biostimulator 100 can then be rotated in the right-handed direction to screw the helix into the tissue. The fixation element 114 may alternatively have a left-handed spiral direction to enable the biostimulator 100 to be screwed into the target tissue via left-handed rotation.

In an embodiment, the helix mount 112 may be positioned between the fixation element 114 and the flange 302. The helix mount 112 can electrically isolate the fixation element 114 from the feedthrough subassembly 204. For example, the helix mount 112 can be formed from an insulating material, such as polyetheretherketone (PEEK) to reduce the likelihood of electrical shorting between the helix 114 and the electrode 104 or the flange 302. The insulating material of the helix mount 112 may also be rigid to mechanically support the fixation element 114 during advancement into the target tissue.

The biostimulator 100 can be implanted in a body region having fluids, e.g., within the blood of a heart chamber, and thus, portions of the biostimulator 100 can be sealed and/or protected against fluid ingress that may compromise functionality of the biostimulator 100. For example, portions of the electrical feedthrough subassembly 204, such as the flange 302, may be coated with a protective coating to prevent short circuiting of the distal electrode 104 and the proximal electrode 106. In one implementation, the distal electrode 104 is spatially near the flange 302, which can be a portion of the proximal electrode 106. Thus, if blood were allowed to fill the gap between the distal electrode 104 and the flange 302, the electrodes 104, 106 could be electrically shorted and pacing impulses may not properly pace the cardiac tissue. Accordingly, a barrier can be included in the biostimulator 100 to prevent blood from filling a cavity within the biostimulator between the distal electrode 104 and the proximal electrode 106.

Figure 7:
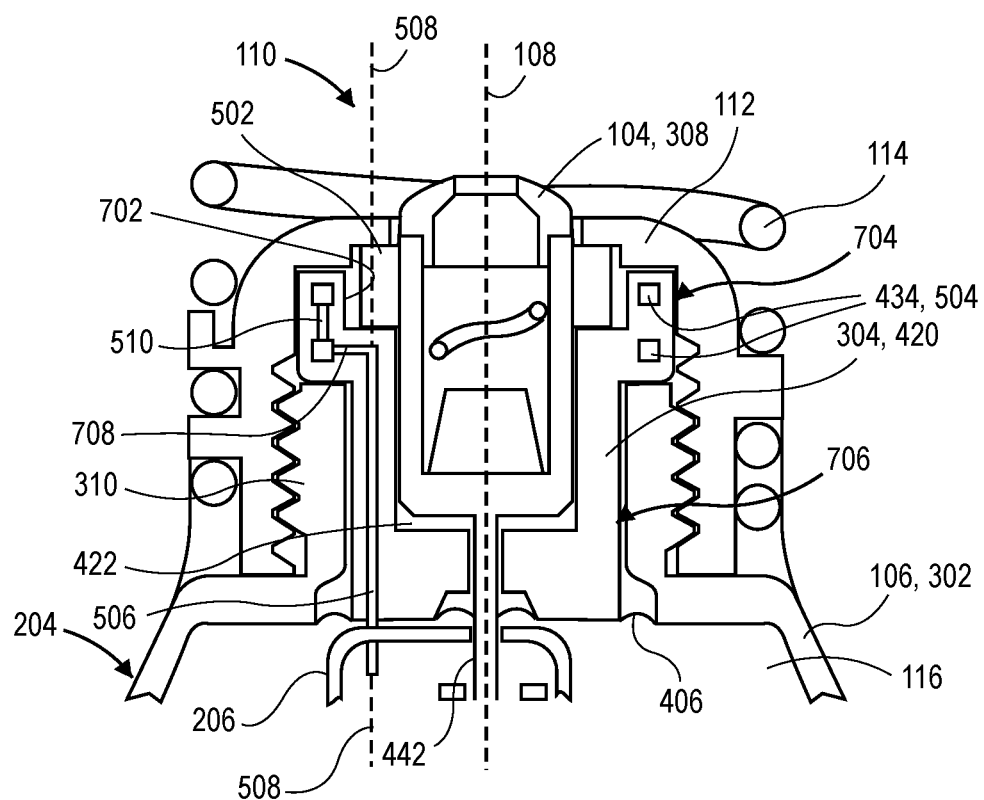
FIG. 7 is a cross-sectional view of a header assembly of a biostimulator, in accordance with an embodiment.

In one implementation, the barrier is provided by a gasket 502. The gasket 502 can be resiliently compressed between the helix mount 112 and one of the flange 302 (FIG. 5) or the insulator 304 (FIG. 7). More particularly, the gasket 502 can have an annular body, e.g., an o-ring shape, and the annular body can be resiliently compressed between the helix mount 112 and either the flange 302 or the insulator 304. The annular body of the gasket 502 can extend around the electrode 104. For example, the annular body can extend circumferentially about the cup 440. Accordingly, the gasket 502 can fill a gap between a proximal surface of the helix mount 112 and a distal face or surface of the electrical feedthrough subassembly 204. The compressed gasket 502 can form a seal against the compressing surfaces to fill the gap between the distal electrode 104 and the proximal electrode 106 (e.g., the flange 302). Therefore, the gasket 502 can separate and protect the conductive surfaces of the biostimulator 100 from short circuiting.

Still referring to FIG. 5, in an embodiment, the gasket 502 is resiliently compressed between the helix mount 112 and the flange 302, and the gasket 502 extends around the insulator wall 420. A radially inward surface of the annular body can press against the insulator wall 420 to form a seal around the insulator 304. Accordingly, ingress of fluid from a gap between the helix mount 112 and the electrode tip 308 toward the flange 302 may be prevented.

The antenna 434 can be embedded in the insulator wall 420 as described above. The antenna 434 may have one or more antenna loops 504 located within the insulator wall 420 between the insulator distal end 430 and the insulator proximal end 432. The dielectric constant of the ceramic material surrounding the metallic antenna loops 504 can allow the antenna 434 to be much smaller than the typical ribbon antennas used in conventional pacemakers. Accordingly, the antenna 434 can occupy minimal space, and does not require an increase in the overall device size.

In an embodiment, the antenna loop(s) extend around the longitudinal axis 108. For example, the one or more loops may include several loops extending circumferentially around the electrode 104 disposed within the insulator cavity 422. In any case, the loops may have a circular pattern within respective transverse planes oriented perpendicular to the longitudinal axis 108.

The one or more antenna loops 504 can be embedded in the insulator wall 420 distal to the flange distal end 412.

More particularly, the insulator distal end 430 can be distal to the flange distal end 412, and the antenna loops 504 can be located longitudinally between the insulator distal end 430 and the flange distal end 412. It will be appreciated that locating the antenna loops 504 distal to, e.g., vertically above, the flange distal end 412 can reduce interference from the metallic mounting wall 310, and accordingly, may optimize a communication range of the antenna 434.

The antenna 434 can include an antenna lead 506 extending longitudinally from the antenna loops 504. In an embodiment, the antenna lead 506 is connected to a lower antenna loop at a distal end and extends from the lower antenna loop along a lead axis 508. The lead axis 508 can extend longitudinally, e.g., parallel to the longitudinal axis 108. Accordingly, the antenna lead 506 can extend through the insulator wall 420 and outward from the insulator proximal end 432. In an embodiment, the antenna lead 506 extends into the electronics compartment 116 and electrically connects to electronic circuitry 206 contained within the electronics compartment 116. Accordingly, communication circuitry can use the antenna 434 to communicate wirelessly with an external communication device.

In addition to the antenna lead 506, the antenna 434 can include electrical connectors to interconnect the various antenna components. For example, the lower antenna loop can be connected to an adjacent (or an upper) antenna loop through an antenna via 510. The antenna via 510 can extend vertically to interconnect the stacked loops. Alternative electrical connectors to interconnect the various antenna components can include lateral traces (FIG. 7).

Figure 6:
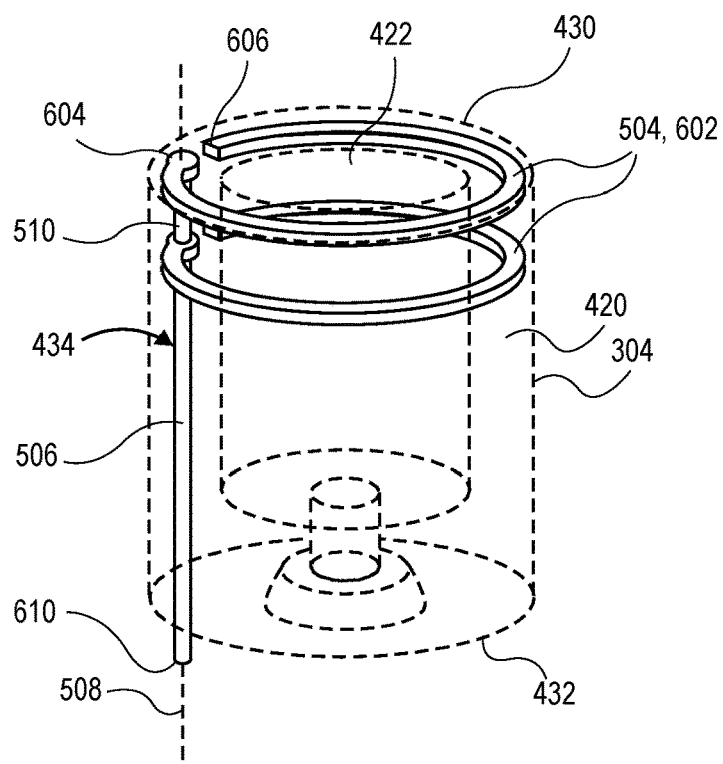
FIG. 6 is a perspective view of an insulator for a header assembly of a biostimulator, in accordance with an embodiment.

Referring to FIG. 6, a perspective view of an insulator for a header assembly of a biostimulator is shown in accordance with an embodiment. The insulator 304 is shown in dashed lines to improve visibility of the embedded antenna 434. The antenna 434 may be a monopole antenna. More particularly, the one or more antenna loops 504 can include one or more open loops 602. The open loops 602 can be c-shaped and extend from respective first ends 604 to respective second ends 606. The first ends can be connected to the antenna lead 506 (or to the antenna via 510). By contrast, the second ends 606 can be free ends. The c-shaped profile of the open loops 602 may have a width dimension that is greater than a width of the insulator cavity 422 and less than a width of the insulator wall 420. More particularly, the open loops 602 may be fully embedded within the insulator wall 420. Alternatively, a portion of the antenna loops 504 may be exposed from the insulator wall 420. For example, the first ends 604 may be exposed and the second ends 606 may be embedded.

The first end 604 and the second end 606 of each loop 504 can be within a same transverse plane. More particularly, the loops may be horizontally configured and vertically stacked. The horizontal orientation of the antenna loop 504 provides for the loop profile to be perpendicular to the lead axis 508. Accordingly, the antenna lead 506 can intersect and extend perpendicular to the antenna loops 504. The antenna lead 506 can be coaxial with, or laterally offset from, the antenna via 510. The lead and the via may be embedded or exposed from the insulator wall 420. As shown, the lead 506 can extend from the loops to a free end 610 that is exposed below the insulator wall 420. More particularly, the free end 610 may be proximal to the insulator proximal end 432. The free end 610 can connect to the electronic circuitry 206.

Referring to FIG. 7, a cross-sectional view of a header assembly of a biostimulator is shown in accordance with an embodiment. The header assembly 110 of FIG. 7 can have similar or identical components and features to the header assembly 110 of FIG. 5. In an embodiment, however, rather than being located external to the insulator 304, the gasket 502 can be located internal to the insulator 304. The gasket 502 can therefore be resiliently compressed between the helix mount 112 and the insulator 304 to seal against the ingress of fluid toward the flange 302. Furthermore, the gasket 502 may extend around the electrode 104, and thus, the gasket 502 may be resiliently compressed between the helix mount 112 and the electrode 104.

In an embodiment, the insulator cavity 422 includes a counterbore 702. For example, the insulator 304 can have a distal section 704 and a proximal section 706, and the counterbore 702 can be in the distal section 704. The counterbore 702 can be a flat-bottomed hole, and the bottom of the counterbore 702 can be a top surface of the insulator wall 420 extending over the proximal section 706. The gasket 502 may be disposed within the counterbore 702. The gasket 502 can be compressed vertically between a bottom surface of the helix mount 112 and the top surface of the proximal section 706 of the insulator wall 420. The compressed gasket 502 within the counterbore 702 ensures electrical isolation between the tip electrode 104 and the flange 302.

The antenna 434 can be embedded within the distal section 704 of the insulator wall 420. As described above, the distal section 704 containing the antenna 434 can protrude out of the flange 302 such that the antenna loops 504 are positioned for optimal communication range. Furthermore, since the distal section 704 can extend radially outward from the proximal section 706, the antenna loops 504 may be vertically above the mounting wall 310. Accordingly, the antenna loops 504 of the embodiment illustrated in FIG. 7 may be wider than the antenna loops 504 of the embodiment illustrated in FIG. 5.

Whereas the antenna loops 504 may be embedded within the wider distal section 704 of the insulator wall 420, the antenna lead 506 may be embedded within the narrower proximal section 706 of the insulator wall 420. As such, the antenna lead 506 may be radially inward from the antenna loops 504, and accordingly, the lead axis 508 can extend longitudinally through (radially inward of) the one or more loops. For example, the lead axis 508 can extend perpendicular to the transverse planes containing the antenna loops 504 and through the areas contained by the antenna loops 504 within the transverse planes. The antenna lead 506 can extend through a length of the insulator 304 to the electronic circuitry 206 contained within the electronics compartment 116.

The antenna loops 504 can include several stacked loops, as described above, and the loops can be interconnected by the antenna via 510. Similarly, the lower antenna loop 504 can be connected to a distal end of the antenna lead 506 by a lateral trace 708. More particularly, the lateral trace 708 can extend transversely inward from the lower antenna loop 504 to the antenna lead 506.

Figure 8:
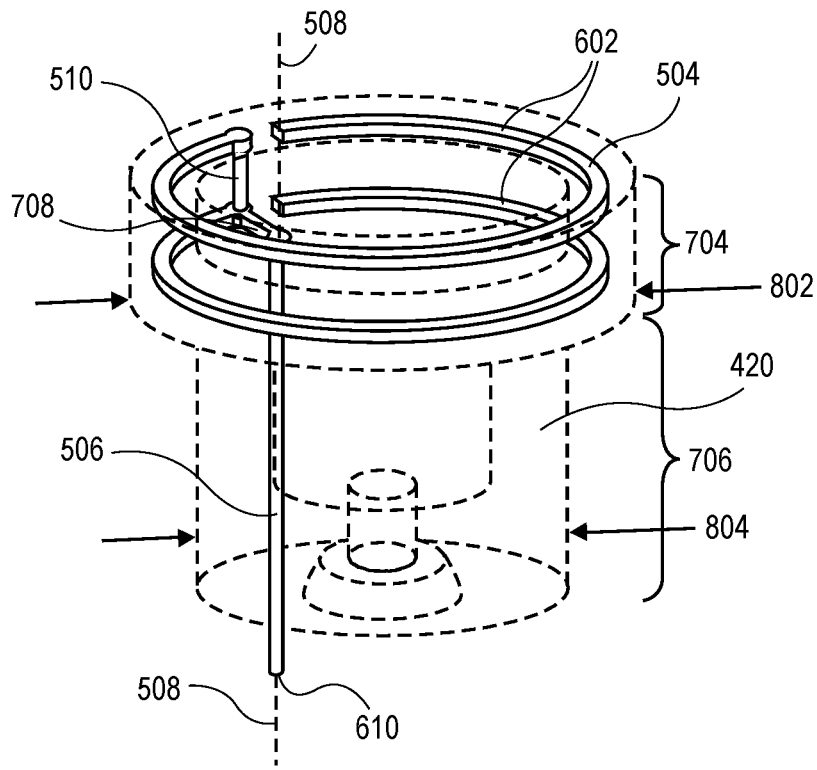
FIG. 8 is a perspective view of an insulator for a header assembly of a biostimulator, in accordance with an embodiment.

Referring to FIG. 8, a perspective view of an insulator for a header assembly of a biostimulator is shown in accordance with an embodiment. As described above, the insulator wall 420 includes the distal section 704 having a first transverse width 802 larger than a second transverse width 804 of the proximal section 706 of the insulator wall 420. The antenna loops 504 embedded in the wider distal section 704 can be open loops 602 to provide a monopole antenna 434. The open loops 602 can be connected to the antenna lead 506, which is embedded within the narrower proximal section 706. A lateral trace 708 can extend laterally from the loops to the lead to interconnect the components. Thus, the antenna loops 504 can be mounted above the mounting wall 310, and the antenna lead 506 can extend through the flange cavity 406 parallel to the pin 442 that carries electrical impulses to and from the electronic circuitry 206. Accordingly, communication signals and pacing impulses can be simultaneously transmitted from the electronic circuitry 206 to locations distal to the flange 302 through the electrical feedthrough subassembly 204.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. An insulator for a header assembly of a biostimulator, comprising:
   an insulator wall extending around an insulator cavity, wherein the insulator cavity extends along a longitudinal axis from an insulator distal end of the insulator wall to an insulator proximal end of the insulator wall; and
   an antenna including one or more antenna loops embedded in the insulator wall between the insulator distal end and the insulator proximal end, and an antenna lead extending from the one or more antenna loops through the insulator proximal end to a free lead end.

2. The insulator of claim 1, wherein the insulator includes a ceramic material.

3. The insulator of claim 1, wherein the one or more antenna loops include one or more open loops having respective free loop ends.

4. The insulator of claim 3, wherein the one or more open loops include a plurality of open loops extending around the longitudinal axis.

5. The insulator of claim 3, wherein the antenna lead has a lead axis extending longitudinally through the one or more antenna loops, and wherein a lateral trace extends transversely inward from the one or more antenna loops to the antenna lead.

6. The insulator of claim 1, wherein a distal section of the insulator wall has a first transverse width larger than a second transverse width of a proximal section of the insulator wall.

7. A header assembly for a biostimulator, comprising:
   a flange including a mounting wall extending around a flange cavity, wherein the mounting wall has a flange distal end; and
   an insulator within the flange cavity and including
      an insulator wall extending around an insulator cavity, wherein the insulator cavity extends along a longitudinal axis from an insulator distal end of the insulator wall to an insulator proximal end of the insulator wall, and
      an antenna including one or more antenna loops embedded in the insulator wall distal to the flange distal end, and an antenna lead extending from the one or more antenna loops through the insulator proximal end to a free lead end.

8. The header assembly of claim 7 further comprising an electrode within the insulator cavity, wherein the one or more antenna loops extend around the electrode.

9. The header assembly of claim 8 further comprising:
   a helix mount mounted on the flange; and
   a gasket having an annular body extending around the electrode, wherein the annular body is resiliently compressed between the helix mount and one of the flange or the insulator.

10. The header assembly of claim 9, wherein the gasket is resiliently compressed between the helix mount and the flange, and wherein the annular body extends around the insulator wall.

11. The header assembly of claim 9, wherein a distal section of the insulator wall has a first transverse width larger than a second transverse width of a proximal section of the insulator wall, and wherein the gasket is resiliently compressed between the helix mount and the insulator.

12. The header assembly of claim 11, wherein the insulator cavity includes a counterbore in the distal section, and wherein the gasket is disposed within the counterbore.

13. A biostimulator, comprising:
   a housing having an electronics compartment;
   a flange mounted on the housing and including a mounting wall extending around a flange cavity; and
   an insulator within the flange cavity and including
      an insulator wall extending around an insulator cavity, wherein the insulator cavity extends along a longitudinal axis from an insulator distal end of the insulator wall to an insulator proximal end of the insulator wall, and
      an antenna including one or more antenna loops embedded in the insulator wall between the insulator distal end and the insulator proximal end, and an antenna lead extending from the one or more antenna loops through the insulator proximal end to a free lead end.

14. The biostimulator of claim 13, wherein the one or more antenna loops include a plurality of open loops extending around the longitudinal axis.

15. The biostimulator of claim 14, wherein the antenna lead has a lead axis extending longitudinally through the one or more antenna loops, and wherein a lateral trace extends transversely inward from the one or more antenna loops to the antenna lead.

16. The biostimulator of claim 13 further comprising an electrode within the insulator cavity, wherein the one or more antenna loops extend around the electrode.

17. The biostimulator of claim 16 further comprising:
   a helix mount mounted on the flange; and
   a gasket having an annular body extending around the electrode, wherein the annular body is resiliently compressed between the helix mount and one of the flange or the insulator.

18. The biostimulator of claim 17, wherein a distal section of the insulator wall has a first transverse width larger than a second transverse width of a proximal section of the insulator wall.

19. The biostimulator of claim 18, wherein the insulator cavity includes a counterbore in the distal section, and wherein the gasket is disposed within the counterbore.

20. The biostimulator of claim 13, wherein the antenna lead is electrically connected to electronic circuitry contained within the electronics compartment.

* * * * *